US008465413B2

(12) United States Patent
Deitch et al.

(10) Patent No.: US 8,465,413 B2
(45) Date of Patent: Jun. 18, 2013

(54) METHOD OF TREATING PEYRONIE'S DISEASE

(75) Inventors: Sarah J. Deitch, Minneapolis, MN (US); Janell Colley, Minneapolis, MN (US); Julie M. Kerkvliet, Otsego, MN (US); Gregg Ledin, Aitkin, MN (US)

(73) Assignee: Coloplast A/S, Humlebaek (DK)

( * ) Notice: Subject to any disclaimer, the term of this patent is extended or adjusted under 35 U.S.C. 154(b) by 229 days.

(21) Appl. No.: 12/954,633

(22) Filed: Nov. 25, 2010

(65) Prior Publication Data

US 2012/0136206 A1 May 31, 2012

(51) Int. Cl.
*A61F 5/00* (2006.01)

(52) U.S. Cl.
USPC .......................................... 600/38

(58) Field of Classification Search
USPC ................. 600/38–41; 128/897, 898
See application file for complete search history.

(56) References Cited

U.S. PATENT DOCUMENTS

| 4,175,554 | A | 11/1979 | Gerow |
| 4,338,300 | A | 7/1982 | Gelbard |
| 5,094,230 | A | 3/1992 | Clark, Jr. |
| 5,312,621 | A | 5/1994 | Berman et al. |
| 5,366,729 | A | 11/1994 | Marklund et al. |
| 5,628,329 | A | 5/1997 | Bennett et al. |
| 5,769,088 | A | 6/1998 | Place |
| 5,782,621 | A | 7/1998 | Harris |
| 5,788,627 | A | 8/1998 | Subrini |
| 5,836,864 | A | 11/1998 | Clark, Jr. |
| 6,022,539 | A | 2/2000 | Wegman |
| 6,033,374 | A | 3/2000 | Miller, Jr. |
| 6,113,939 | A | 9/2000 | Place et al. |
| 6,303,126 | B1 | 10/2001 | Nakamura et al. |
| 6,312,720 | B1 | 11/2001 | Katinger et al. |
| 7,056,953 | B2 | 6/2006 | Reddy et al. |
| 7,135,279 | B2 | 11/2006 | Kent et al. |
| 7,780,591 | B2 * | 8/2010 | Egydio ........................ 600/40 |
| 2003/0161821 | A1 | 8/2003 | Santana Ribeiro |
| 2004/0018958 | A1 | 1/2004 | Chung |
| 2004/0043026 | A1 | 3/2004 | Tuan et al. |
| 2004/0077970 | A1 | 4/2004 | Osbon et al. |
| 2004/0146494 | A1 | 7/2004 | Santana |
| 2004/0146496 | A1 | 7/2004 | McMichael |
| 2005/0020569 | A1 | 1/2005 | Easterling |
| 2005/0025804 | A1 | 2/2005 | Heller |
| 2005/0025805 | A1 | 2/2005 | Heller et al. |
| 2005/0038044 | A1 | 2/2005 | Koverech et al. |
| 2005/0085486 | A1 | 4/2005 | Gonzalez-Cadavid et al. |
| 2005/0186261 | A1 | 8/2005 | Avelar et al. |

(Continued)

FOREIGN PATENT DOCUMENTS

| AU | 2855189 A | 7/1989 |
| AU | 2004210013 A1 | 8/2004 |

(Continued)

*Primary Examiner* — Samuel Gilbert
(74) *Attorney, Agent, or Firm* — Coloplast Corp., Coloplast A/S; Nick Baumann

(57) ABSTRACT

A method of treating Peyronie's disease manifested in an erect penis having a first penis side with an unaffected length and a second penis side with an affected length that is shorter than the unaffected length includes attaching an elastic device subcutaneously to the first penis side; and providing the elastic device with a stretch stop that limits elongation of the first penis side to an erection distance that is approximately equal to the affected length of the erect penis.

5 Claims, 8 Drawing Sheets

U.S. PATENT DOCUMENTS

| | | |
|---|---|---|
| 2005/0192210 A1 | 9/2005 | Rothbard et al. |
| 2006/0093690 A1 | 5/2006 | Almagro |
| 2006/0177837 A1 | 8/2006 | Borozan et al. |
| 2006/0228358 A1 | 10/2006 | Lawson et al. |
| 2006/0228775 A1 | 10/2006 | Collier et al. |
| 2007/0016107 A1 | 1/2007 | Egydio |
| 2007/0042938 A1 | 2/2007 | Ansorge et al. |
| 2007/0044163 A1 | 2/2007 | Fagan et al. |
| 2007/0065368 A1 | 3/2007 | Gomer et al. |
| 2007/0065866 A1 | 3/2007 | Gomer et al. |
| 2007/0129600 A1 | 6/2007 | Osbon et al. |
| 2007/0135335 A1 | 6/2007 | Collier et al. |
| 2007/0154481 A1 | 7/2007 | Gelinas et al. |
| 2007/0185203 A1 | 8/2007 | Rothbard et al. |
| 2007/0202077 A1 | 8/2007 | Brodsky et al. |
| 2007/0213681 A1 | 9/2007 | Manna et al. |
| 2007/0219119 A1 | 9/2007 | McMichael |
| 2007/0232649 A1 | 10/2007 | Reddy et al. |
| 2007/0286856 A1 | 12/2007 | Brown et al. |
| 2007/0299088 A1 | 12/2007 | Haning |
| 2008/0107646 A1 | 5/2008 | Chung et al. |
| 2008/0125486 A1 | 5/2008 | Sanchez et al. |
| 2008/0181872 A1 | 7/2008 | Doroudchi |
| 2010/0130816 A1 | 5/2010 | Gekhter |
| 2010/0256444 A1 * | 10/2010 | Egydio .................... 600/40 |

FOREIGN PATENT DOCUMENTS

| | | |
|---|---|---|
| AU | 2004279475 A1 | 4/2005 |
| AU | 2005210668 A1 | 8/2005 |
| AU | 2005253966 A1 | 12/2005 |
| AU | 2005270446 A1 | 2/2006 |
| AU | 2006259113 A1 | 12/2006 |
| AU | 2006269488 A1 | 1/2007 |
| AU | 2006320162 A1 | 6/2007 |
| AU | 2006323490 A1 | 6/2007 |
| AU | 2007214668 A1 | 8/2007 |
| BR | PI9801985 A | 2/2000 |
| BR | PI0006719 A | 9/2001 |
| BR | PI0101823 A | 9/2001 |
| BR | PI0304395 A | 5/2005 |
| BR | PI0601884 A | 9/2006 |
| CA | 2040914 A1 | 10/1991 |
| CA | 2352552 A1 | 10/1991 |
| CA | 2137378 A1 | 12/1993 |
| CA | 2186382 A1 | 10/1995 |
| CA | 2204493 A1 | 5/1996 |
| CA | 2339003 A1 | 2/2000 |
| CA | 2366750 A1 | 10/2000 |
| CA | 2443018 A1 | 10/2002 |
| CA | 2509241 A1 | 7/2004 |
| CA | 2509392 A1 | 7/2004 |
| CA | 2514071 A1 | 8/2004 |
| CA | 2541438 A1 | 4/2005 |
| CA | 2536096 A1 | 8/2005 |
| CA | 2569705 A1 | 12/2005 |
| CA | 2575907 A1 | 2/2006 |
| CA | 2618939 A1 | 4/2006 |
| CA | 2498639 A1 | 9/2006 |
| CA | 2611386 A1 | 12/2006 |
| CA | 2627873 A1 | 5/2007 |
| DK | 455789 | 9/1989 |
| EA | 004801 B1 | 8/2004 |
| EP | 1574213 A1 | 9/2005 |
| ES | 2197018 A1 | 12/2003 |
| FR | 2727855 A1 | 6/1996 |
| GB | 9225475 | 1/1993 |
| GB | 200130720 | 2/2002 |
| GB | 200303337 | 3/2003 |
| GB | 200425633 | 12/2004 |
| GB | 200614608 | 8/2006 |
| IT | RM20010695 | 11/2001 |
| RU | 2234257 C2 | 8/2004 |
| RU | 2256405 C1 | 7/2005 |
| RU | 2326602 C1 | 6/2008 |
| WO | 93/25667 A1 | 12/1993 |
| WO | 95/05134 A1 | 2/1995 |
| WO | 95/26158 A1 | 10/1995 |
| WO | 95/29694 A1 | 11/1995 |
| WO | 96/14083 A1 | 5/1996 |
| WO | 00/07587 A1 | 2/2000 |
| WO | 00/59495 A1 | 10/2000 |
| WO | 02/074329 A1 | 9/2002 |
| WO | 02/080962 A1 | 10/2002 |
| WO | 2004/037183 A1 | 5/2004 |
| WO | 2004/058292 A2 | 7/2004 |
| WO | 2004/059318 A2 | 7/2004 |
| WO | 2004/069866 A1 | 8/2004 |
| WO | 2004/086981 A1 | 10/2004 |
| WO | 2005/003351 A1 | 1/2005 |
| WO | 2005/004906 A2 | 1/2005 |
| WO | 2005/014634 A1 | 2/2005 |
| WO | 2005/035548 A1 | 4/2005 |
| WO | 2005/074913 A2 | 8/2005 |
| WO | 2005/123077 A2 | 12/2005 |
| WO | 2006/015715 A1 | 2/2006 |
| WO | 2006/044017 A2 | 4/2006 |
| WO | 2006/123226 A2 | 11/2006 |
| WO | 2006/134101 A2 | 12/2006 |
| WO | 2007/008486 A2 | 1/2007 |
| WO | 2007/053573 A2 | 5/2007 |
| WO | 2007/059119 A2 | 5/2007 |
| WO | 2007/065167 A1 | 6/2007 |
| WO | 2007/066082 A1 | 6/2007 |
| WO | 2007/093409 A2 | 8/2007 |
| WO | 2008/016682 A2 | 2/2008 |
| WO | 2008/020027 A2 | 2/2008 |
| WO | 2008/020028 A1 | 2/2008 |
| WO | 2008/020030 A1 | 2/2008 |
| WO | 2008/020039 A2 | 2/2008 |
| WO | 2008/020040 A2 | 2/2008 |
| WO | 2008/060783 A2 | 5/2008 |
| WO | 2008/076270 A2 | 6/2008 |

* cited by examiner

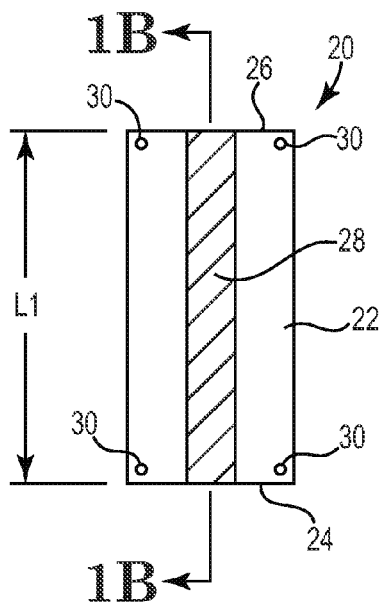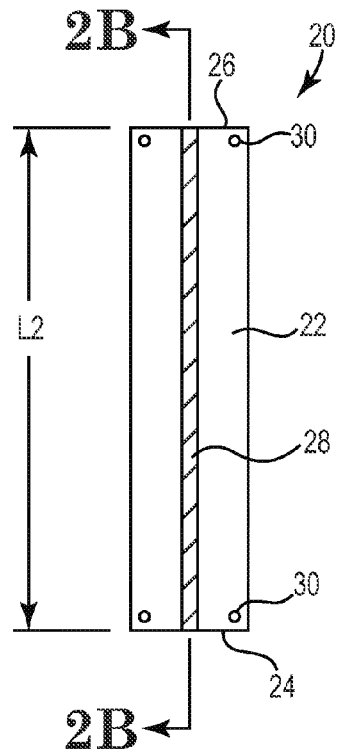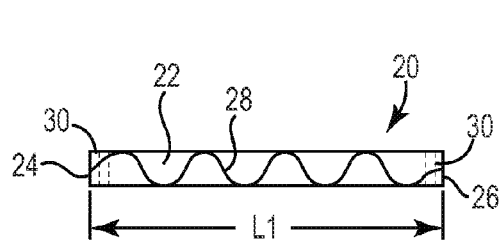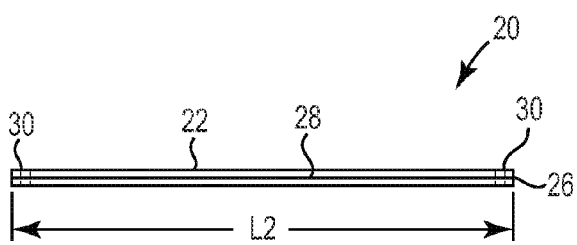
Fig. 1A  Fig. 2A
Fig. 1B  Fig. 2B

METHOD OF TREATING PEYRONIE'S DISEASE

BACKGROUND

Peyronie's disease is manifested by an abnormal bend that occurs in the erect penis of the sufferer and can be associated with painful erection and/or painful intercourse.

Peyronie's disease is related to the development of scar tissue, or plaques, that form on tissues (e.g., tunica albuginea) inside the penis. One non-surgical approach for the treatment of Peyronie's disease includes injecting drugs into the plaques that lessen the compression applied by the plaques to the erect penis. The research and efficacy of this approach is limited.

Surgical treatments for Peyronie's disease include excising portions of the tunica albuginea from the penis opposite the plaque and closing the fenestrations with sutures. Access to the tunica albuginea is achieved by first degloving the penile skin away from the penis to expose the Buck's fascia and tunica albuginea along the length of the penis. Degloving the penile skin is painful and the recovery time for the patient can be several weeks. Although the long term results of this surgical approach are good, both short term (within 8 weeks) and long term failures can present with residual penile deformity.

Another surgical treatment includes corporal plication in which plication sutures are placed on the contralateral side of the plaque without excising the tunica albuginea or removing the plaque. Corporal plication is most commonly employed subsequent to a previous Peyronie's treatment surgery to correct small angles of residual penile deformity.

Patients and clinicians desire more effective and less invasive surgical treatments for Peyronie's disease.

SUMMARY

One aspect provides a Peyronie's treatment device configured to treat an erect penis having curvature characterized by a first penis side with an unaffected length and a second penis side with an affected length that is shorter than the unaffected length. The device includes a band connected between a proximal support that is attachable to a base of a penis and a distal support that is attachable adjacent a corona of the penis. The band has an elastic material and a second material that is attached to the elastic material. The second material is provided to stop elongation of the elastic material at a length approximately equal to the affected length of the erect penis.

One aspect provides a method of treating Peyronie's disease manifested in an erect penis having a first penis side with an unaffected length and a second penis side with an affected length that is shorter than the unaffected length. The method includes attaching an elastic device subcutaneously to the first penis side; and providing the elastic device with a stretch stop that limits elongation of the first penis side to an erection distance that is approximately equal to the affected length of the erect penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is a top view and FIG. 1B is a cross-sectional view of one embodiment of a Peyronie's treatment device having an elastic material in a relaxed state.

FIG. 2A is a top view and FIG. 2B is a cross-sectional view of one embodiment of the Peyronie's treatment device illustrated in FIGS. 1A and 1B with the elastic material stopped in a stretched state by a second material that is attached to the elastic material.

DETAILED DESCRIPTION

Figure 3A:
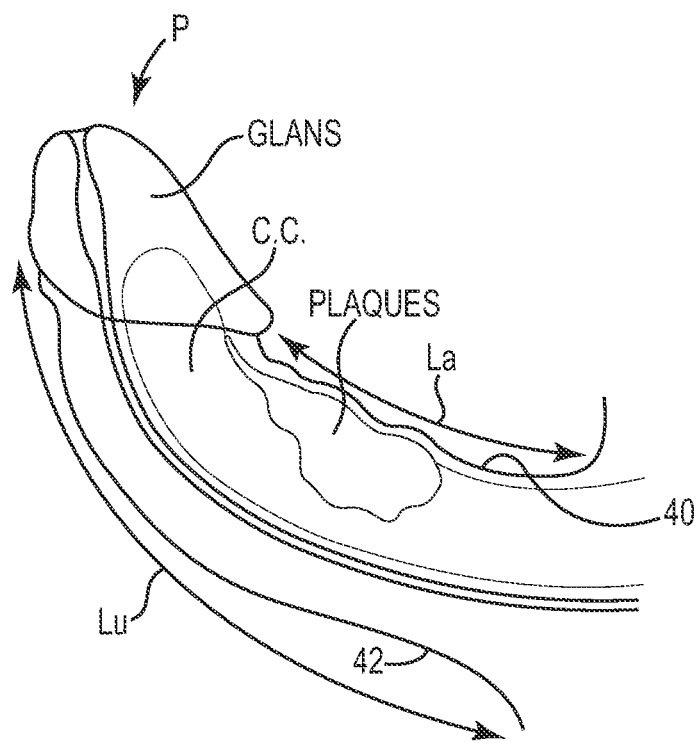
FIG. 3A is a side schematic view of an erect penis afflicted by Peyronie's disease.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Soft tissue includes dermal tissue, sub-dermal tissue, ligaments, tendons, or membranes but does not include bone.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal and of the crus of the penis is located proximal relative to the male body such that a distal end of a corpora cavernosum of the patient extends about midway into the glans penis.

Embodiments provide an internal traction device that treats the effects of Peyronie's disease by reducing the curvature of an erect penis. In one embodiment, the device is attached subcutaneously to an exterior surface of the tunica albuginea on a contralateral side of the penis opposite the side on which the Peyronie's plaques have formed and functions to counteract the asymmetrical contraction of the penis caused by the Peyronie's plaques. The device is fabricated from a stretchy material that accommodates movement of the penis between a flaccid state and an erect state. The device is configured to stretch and elongate up to a built-in stop-limit that is selected to match the length of the penis on the side on which the Peyronie's plaques have formed. In this manner, all sides of the penis elongate to an approximately equal length.

In one embodiment, the device is attached to the tunica albuginea of the penis without incising the tunica or removing the Peyronie's plaques, and thus use of the device limits patient discomfort and reduces the healing time for the Peyronie's-afflicted patient compared to other procedures.

FIG. 1A is a top view and FIG. 1B is a cross-sectional view of one embodiment of a Peyronie's treatment device 20. The Peyronie's treatment device 20 (device 20) is provided as a band 20 that includes an elastic material 22 extending between a proximal support 24 that is attachable to a base of a penis and distal support 26 that is attachable adjacent a corona of the penis, and includes a second material 28 attached to the elastic material 22. In one embodiment, the device 20 provides attachment locations 30 that allow the device 20 to be attached subcutaneously within the penis.

Patients who suffer from Peyronie's disease develop a curvature in the erect penis characterized by one side of the penis having an unaffected length and, generally, an opposite side of the penis having an affected length that is shorter than the unaffected length of the penis. The band 20 provides a length that is selected to stretch between a first initial length L1 extending between a base of the penis and a corona of the penis when the penis is flaccid to a final length L2 (FIG. 2) that is approximately equal to be affected length of the penis. The elastic material 22 is thus configured to move with the penis between its flaccid state and its erect state, and when the penis is erect, the device 20 is configured to straighten the penis to an approximately symmetric shape/length.

In one embodiment, the second material 28 provides a stop for the elastic material 22 that allows the elastic material 22 to stretch from the initial length L1 to the final length L2, where the final length L2 is selected prior to surgery to be approximately equal to the affected length of the Peyronie's-affected erect penis. In one embodiment, the second material 28 provides means for limiting elongation of the stretchable band 20 to a distance that is greater than the affected length of the Peyronie's-affected erect penis.

In one embodiment, the band 20 is elastically deformable between the initial length L1 and the final length L2 and the second material 28 configures the band 20 to be inelastically deformable past the final length L2. That is to say, the band 20 is stretchable up to the final length L2, and if a sufficiently large force is applied to the band 20 to stretch it beyond the length L2, the band will fracture or otherwise break. Thus, the elastic material 22 is stretchable from the initial length L1 that is less than the affected length to a length that is greater than the affected length, and the second material 28 prevents elongation of the elastic material 22 past the affected length.

In one embodiment, the elastic material 22 is provided as a knitted fabric and the second material 28 is provided as a separate fabric 28 that is attached to the knitted fabric 22, where the separate fabric 28 has some limited degree of stretch that allows the elastic material 22 to stretch up to the desired the final length L2 before the separate fabric 28 stops the elongation of the elastic material 22 at the final length L2. The separate fabric 28 thus allows the elastic material 22 to stretch up to but not beyond the final length L2. With this in mind, one embodiment of the band 20 includes stretching the elastic material 22 to the final length L2 and attaching the separate fabric 28 to the elastic material 22. When the elastic material 22 is relaxed the separate fabric 28 moves with the elastic material 22. When the elastic material 22 is stretched, the separate fabric 28 moves to allow the elastic material 22 to stretch up to but not beyond the final length L2.

In one embodiment, the elastic fabric 22 is provided as a knitted fabric and the second material 28 is provided as an inelastic woven fabric that is attached to the knitted fabric. In one embodiment, the inelastic woven fabric 28 has a fixed length generally equal to L2 and is attached to the elastic fabric 22 in a manner (similar to that described above) that allows the elastic material 22 to stretch up to but not beyond the final length L2.

In one embodiment, the elastic material 22 is provided as a knitted fabric and the second material 28 is provided as inelastic strand 28 embedded in the knitted fabric. As an example, the elastic material 22 is stretched to the final length L2 and the inelastic strand 28 is attached to the elastic material 22 to limit its elongation. In one embodiment, the inelastic strand 28 is fixed to the elastic fabric 22 in a manner that allows the elastic material 22 to stretch up to but not beyond the final length L2.

The elastic material 22 is stretchable between the initial length L1 and a length that is longer than the final length L2, and a second material 28 is provided to stop the elongation of the elastic material 22 at the final length L2. The knitted fabrics of the elastic material 22 are suitably fabricated from polymer fiber such as polypropylene, polyethylene, or polyolefin or such fibers coated with slip agents or elastic additives. The second material 28 is suitably fabricated from, as an example, nylon thread(s) woven or otherwise processed to provide a stop to the elongation of the elastic material 22 at the final length L2. The second material 28 is suitably fabricated from an inelastic suture filament.

Knitted fabrics are generally fabricated from a filament that is knit on a path to form a chain of loops, where each loop in the chain of loops is suspended by a neighboring loop. The loops are secured as they are knit by passing a newly formed loop through a previously formed loop. The chain of loops that run in a lateral direction are referred to as a wale, and the path that the knitting filament follows is referred to as a course (see FIG. 4B as an example of a knitted fabric).

A woven material is different from a knitted material in that woven material is formed by threads that run parallel in a lengthwise direction (warp threads) and cross with a separate set of parallel threads placed in a crosswise direction (weft threads). Woven materials can thus be fabricated that have little or no stretch as the warp and weft threads connect together to limit their mutual movement. In contrast, the meandering course that forms the loops of a knitted material provide the knit with greater elasticity (e.g., stretchiness) over the woven material since the loops move within each other.

With the above mind, the device 20 or the band 20 is provided in multiple formats (for example, each with a different final length L2) that allow the surgeon to select the desired final length L2 as based on the affected length of the erect penis of the patient suffering from Peyronie's disease.

FIG. 2A is a top view and FIG. 2B is a cross-sectional view of the Peyronie's treatment device 20 illustrated in FIG. 1 with the elastic material 22 stopped at a desired elongated length by the second material 28.

Figure 3B:
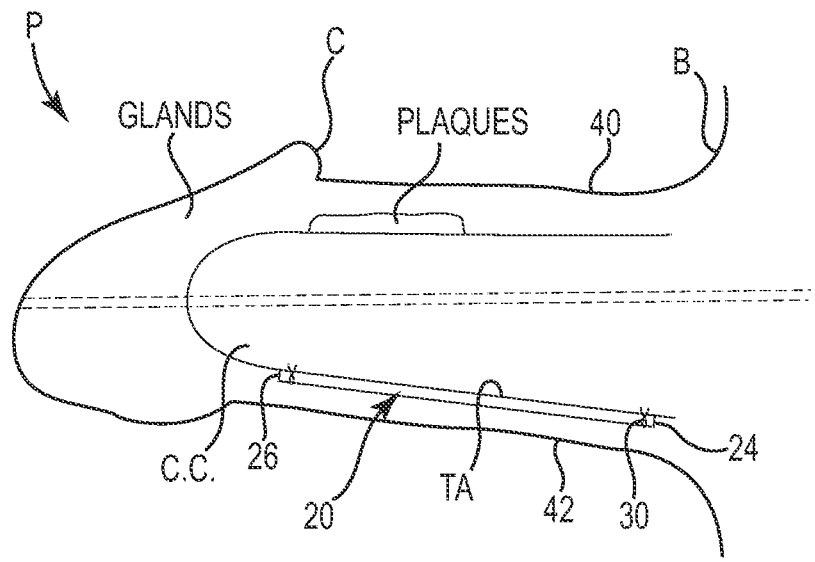
FIG. 3B is a side schematic view of the penis illustrated in FIG. 3A in a flaccid state and including the treatment device illustrated in FIGS. 1A and 1B attached to the tunica albuginea of the penis.
Figure 3C:
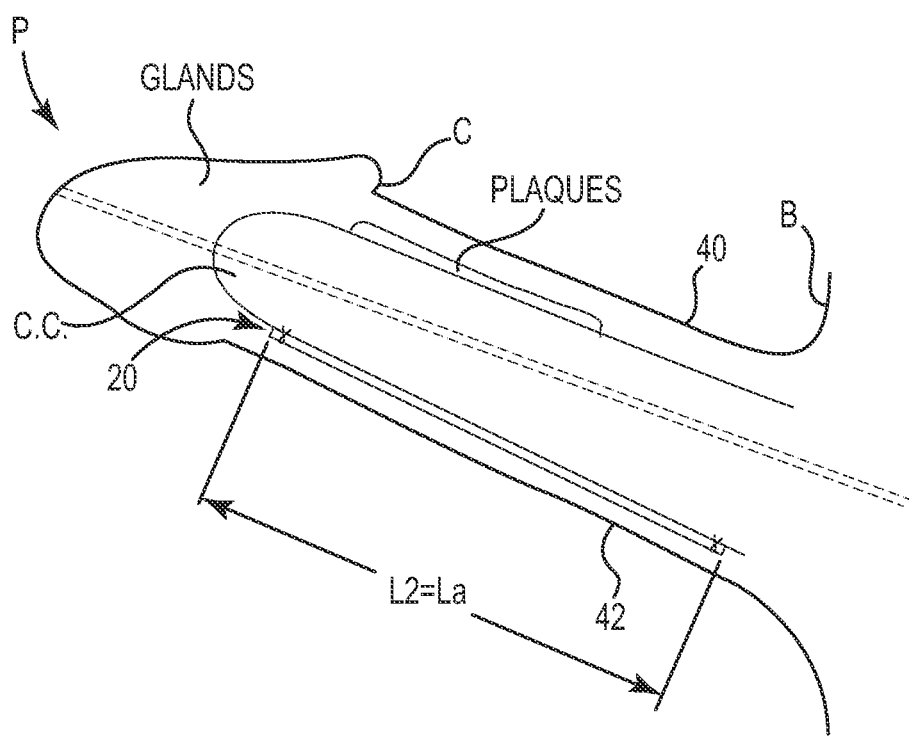
FIG. 3C is a side schematic of the penis illustrated in FIG. 3B in an erect state having reduced curvature as compared to the untreated penis illustrated in FIG. 3A.

FIGS. 3A, 3B, and 3C are schematic views of a penis P.

FIG. 3A is a side schematic view of a Peyronie's afflicted erect penis. The erect penis P has a pair of corpora cavernosa CC that extend from a proximal location internal to the body up to a mid-location of the glans penis. The illustrated erect penis P includes plaques that have formed on an affected side 40 of the penis P that cause the erect penis P to have an affected length La. The penis P has an unaffected side 42 that is generally opposite the affected side 40 of the penis. The unaffected side 42 of the penis P has an unaffected length of Lu. The affected side 40 of the erect penis is generally shorter than the unaffected side 42 of the erect penis such that the erect penis P presents with an undesirable curvature.

FIG. 3B is a side schematic view of the penis P including the band 20 subcutaneously attached to the tunica albuginea TA of the penis P. The tunica albuginea TA of the penis P encapsulates the corpora cavernosa CC. The proximal support 24 of the band 20 is attached to a base B of the penis P and the distal support 26 is attached adjacent to a corona C of the penis P, for example by suturing through the attachment locations 30.

In one embodiment, the band 20 is attached subcutaneously to the tunica albuginea TA of a flaccid penis P. For example, the band 20 is provided in a variety of lengths that allows the surgeon to selective a band 20 having the appropriate initial length L1 and an appropriate final length L2 based on pre-treatment measurements, and knowing these lengths, the surgeon selects the appropriately sized band 20 for attachment to the flaccid penis P.

Alternatively, in one embodiment the band 20 is attached subcutaneously to the tunica albuginea TA of an erect penis P. For example, the surgeon artificially induces an erection in the penis P to observe the angle and extent of the curvature in the Peyronie's affected penis, and after recording this data, selects a band 20 having a final elongated length L2 that is approximately equal to the affected length La of the erect penis. The selected band 20 is attached to the erect penis to provide a suitable amount of correction to the curvature of the Peyronie's affected penis P.

FIG. 3C is a side schematic view of the erect penis P including plaques present on the affected side 40 of the Peyronie's afflicted penis and the band 20 attached subcutaneously to the tunica albuginea to provide a correcting force that resists curvature of the penis P. The erect penis P is thus provided with symmetric sides 40, 42 in which the band 20 configures the unaffected side 42 of the penis P to have a length that is approximately equal to the affected length La of the penis P. As illustrated by FIG. 3C, the final length L2 of the band 20 has a length that is substantially equal to the affected length La of the penis (FIG. 3A).

Figure 4A:
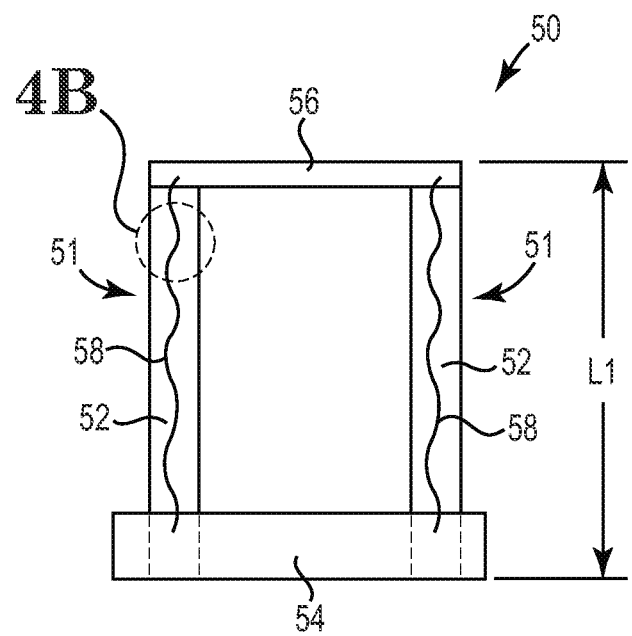
FIG. 4A is a top view of one embodiment of a Peyronie's treatment device in a relaxed, un-stretched state.

FIG. 4A is a top view of one embodiment of a Peyronie's treatment device 50 (device 50). The device 50 is provided with multiple bands 51 having elastic material 52 extending between a proximal support 54 that is attachable to a base of a penis and a distal support 56 that is attachable adjacent a corona of the penis, and a second material 58 attached to the elastic material 52 that is provided to stop elongation of the elastic material 52 at a length approximately equal to the affected length of a Peyronie's affected erect penis.

In one embodiment, the proximal support 54 is provided as a segment that is attachable to less than an entire circumference of the base of the penis P. In one embodiment, the distal support 56 is provided as a segment that is attachable to less than an entire circumference of the penis adjacent the corona.

Figure 4B:
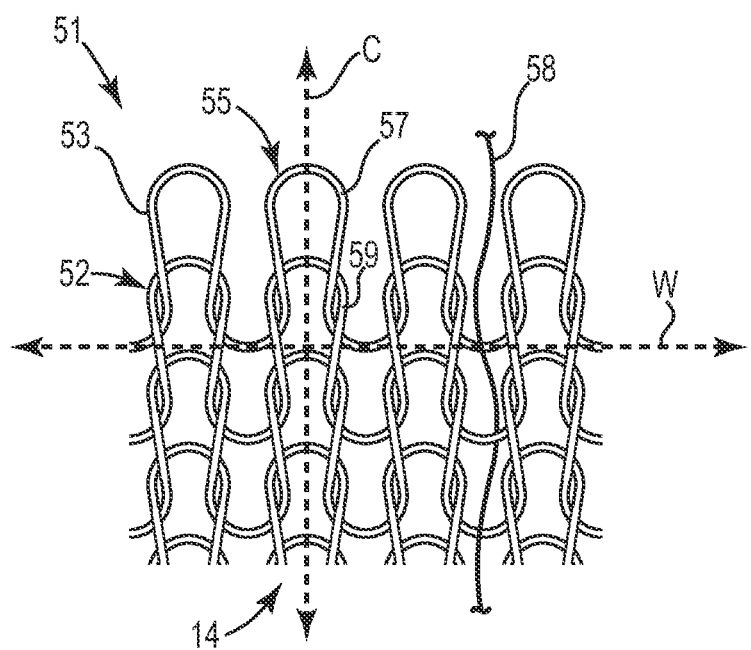
FIG. 4B is a top view of a band of the device illustrated in FIG. 4A showing a stop strand.
Figure 4C:
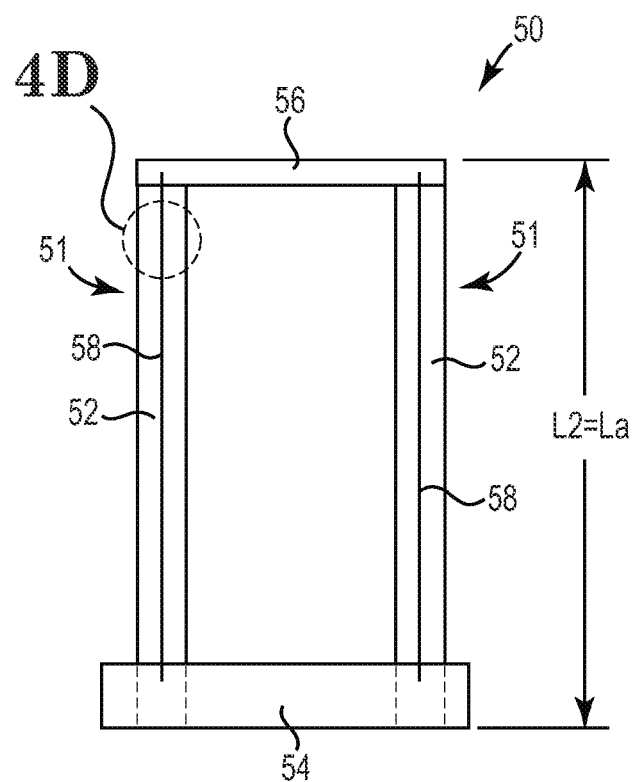
FIG. 4C is a top view of the Peyronie's treatment device illustrated in FIG. 4A in an elongated state.

FIG. 4A illustrates the device 50 having an initial length L1 in a relaxed state and FIG. 4C illustrates the device 50 stretched or elongated to a final length L2 that is selected to be substantially equal to the affected length of an erect Peyronie's affected penis.

FIG. 4B is a top view of one of the bands 51 including a filament 53 knit on a path to form a chain of loops 55, where each loop 57 in the chain of loops 55 is suspended by a neighboring loop 59. In this manner, the loops 55 are secured as they are knit by passing a newly formed loop (e.g., loop 57) through a previously formed loop (e.g., loop 59). The chain of loops that run left-to-right in FIG. 4B are referred to as a wale W. The path that the filament 53 follows is referred to as a course C. In one embodiment, the second material 58 is a strand 58 that is interlaced or woven into the chain of loops 55, where the strand 58 is provided to limit the elongation of the knitted loops in the band 51. In one embodiment, the bands 51 and the strand 58 are each attached on opposing ends between the proximal support 54 and the distal support 56, and when the band 51 is stretched, the strand 58 stops the elongation of the band 51 at the desired length L2.

Figure 4D:
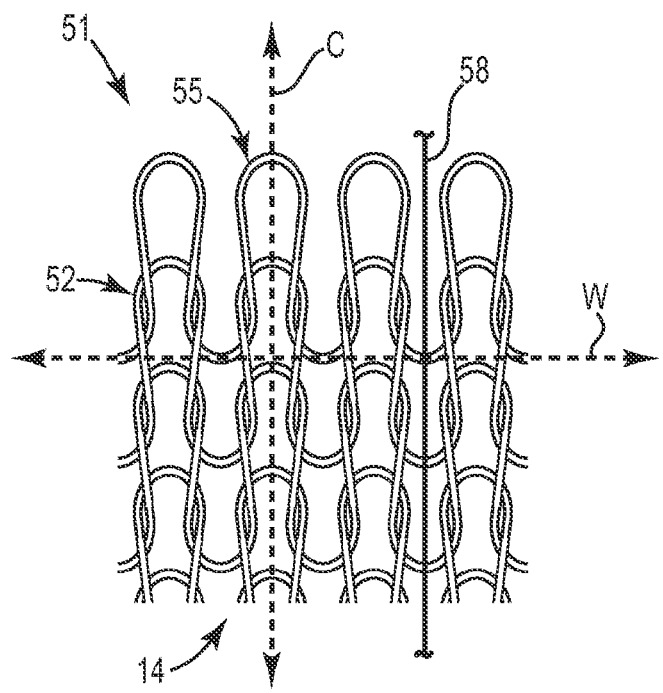
FIG. 4D is a top view of the band of the device illustrated FIGS. 4A and 4C showing the stop strand limiting elongation of the device.

FIG. 4D illustrates the strand 58 stopping the elongation of the device 50 at the final length L2 that is substantially equal to the affected length of an erect Peyronie's affected penis.

Figure 5:
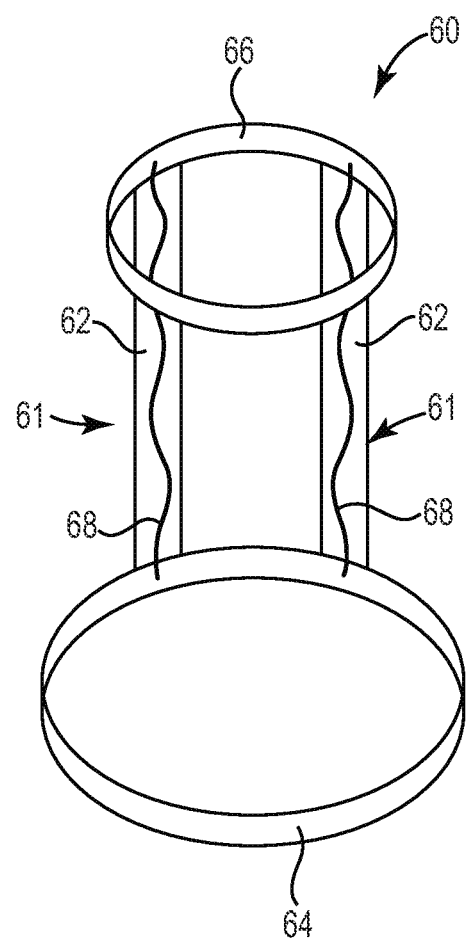
FIG. 5 is a perspective view of one embodiment of a Peyronie's treatment device.

FIG. 5 is a top view of one embodiment of a Peyronie's treatment device 60 (device 60). The device 60 is provided with multiple bands 61 having elastic material 62 extending between a proximal support 64 that is attachable to a base of a penis and a distal support 66 that is attachable adjacent a corona of the penis, and a second material 68 attached to the elastic material 62 that is provided to stop elongation of the elastic material 62 at a length approximately equal to the affected length of a Peyronie's affected erect penis.

In one embodiment, the proximal support 64 is provided as a continuous ring that is attachable around an entire circumference of the base of the penis P and the distal support 66 is provided as a continuous ring that is attachable around an entire circumference of the penis adjacent the corona.

Figure 6:
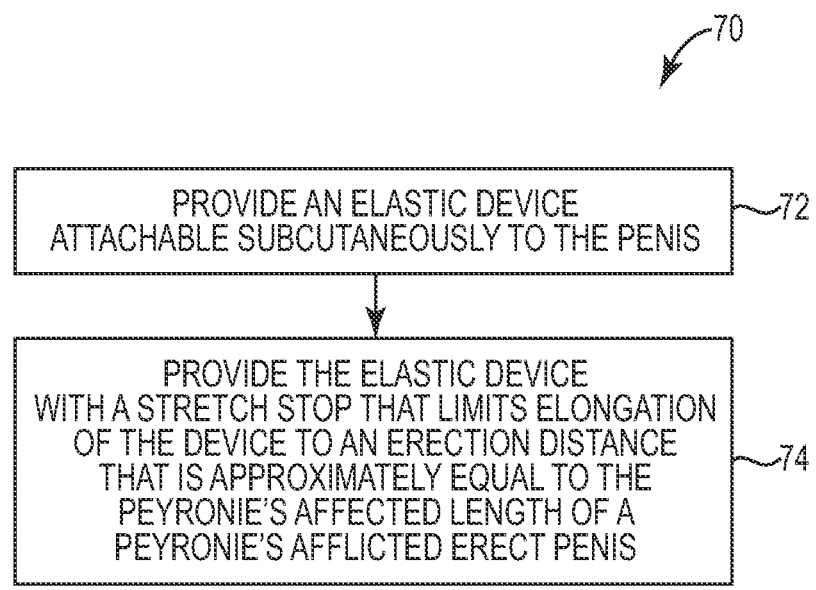
FIG. 6 is a block diagram of one embodiment of a method of treating Peyronie's disease.

FIG. 6 is a block diagram 70 of one embodiment of a method of treating Peyronie's disease. The method of treatment includes at 72 providing an elastic device that is attachable subcutaneously to the penis. The method of treatment includes at 74 providing the elastic device with a stretch stop that limits the elongation of the device to a distance that is approximately equal to the affected length of a Peyronie's afflicted erect penis (see FIG. 3A).

Figure 7:
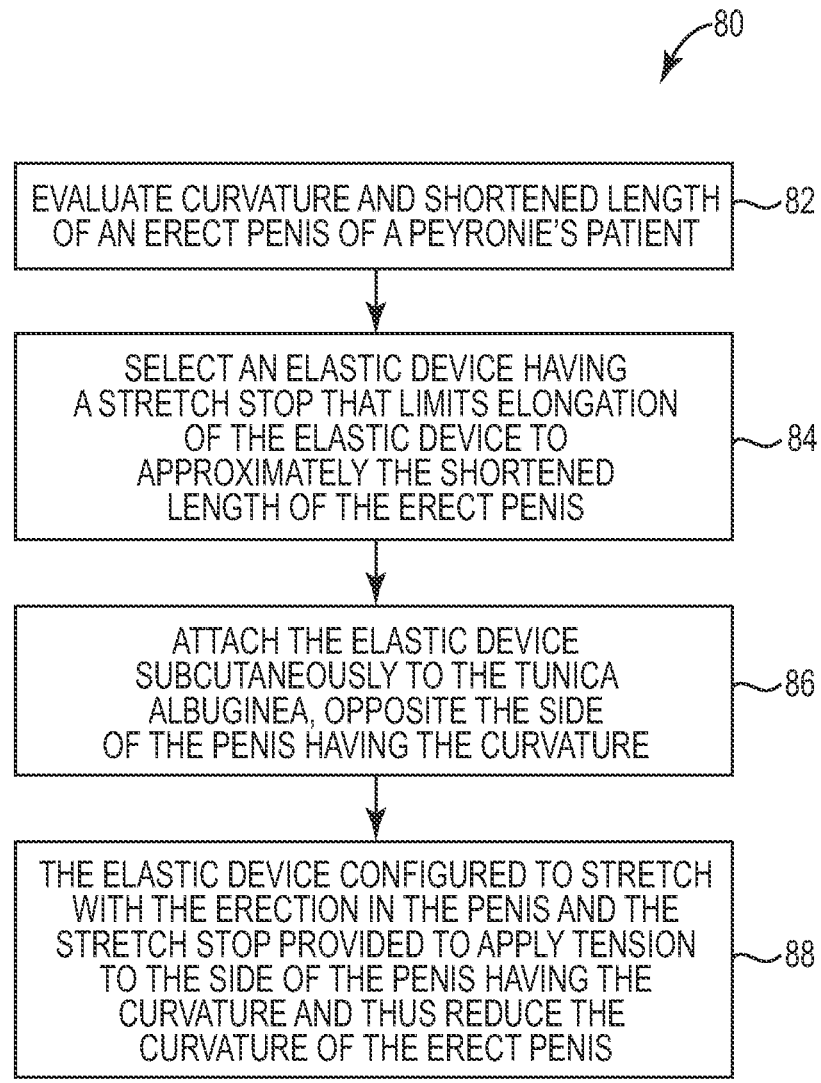
FIG. 7 is a block diagram of one embodiment of a method of treating Peyronie's disease.

FIG. 7 is a block diagram 80 of one embodiment of a method of treating Peyronie's disease. The method of treatment includes at 82 evaluating curvature and a shortened length of an erect penis of a patient afflicted by Peyronie's disease. The method of treatment includes at 84 selecting an elastic device having a stretch stop that limits the elongation of the elastic device to approximately the shortened length of the erect penis. The method of treatment includes at 86 attaching the elastic device to a side of the penis, subcutaneously to the tunica albuginea, opposite the side of the penis having the curvature. The method of treatment includes at 88 configuring the elastic device to stretch with the erection of the penis and configuring the stretch stop to apply tension to the side of the penis having the curvature, thus reducing the curvature of the erect penis.

Example

The following example illustrates, with reference to FIG. 3A, the surgical placement of one of the Peyronie's treatment devices described above without degloving the penile skin.

The patient is anesthetized and surgically draped to define a sterile operating field in an appropriate manner.

The surgeon forms a circumcoronal incision adjacent to the glans penis and a penoscrotal incision adjacent to the base of the penis P. The dartos fascia is reflected to expose the Buck's fascia, and the Buck's fascia is incised down to the tunica albuginea.

The surgeon introduces a flat-bladed tool subcutaneous to the penis over the tunica albuginea and forms a pathway extending from the penoscrotal incision to the circumcoronal incision along the unaffected side 42 of the penis P.

In one embodiment, an artificial erection is imparted to the penis P with an intracavernous injection of saline solution and the surgeon proceeds to attach one of the above-described Peyronie's treatment devices to an exterior surface of the tunica albuginea on a contralateral side of the penis opposite the side on which the Peyronie's plaques have formed.

The proximal support 24 is attached to the base of the penis P, for example with one or more sutures. The flat-bladed tool, or a forceps, is employed to deliver the distal support 26 to a location adjacent a corona of the penis. The surgeon corrects the curvature in the penis P (e.g., manually) and attaches the distal support 26 to the penis at a location that conforms the unaffected side 42 of the penis P to have a length that approximates a length of the affected side 40 of the penis P. In this manner, the implanted Peyronie's treatment device corrects the curvature in the penis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of treating Peyronie's disease manifested in an erect penis having a first penis side with an unaffected length and a second penis side with an affected length that is shorter than the unaffected length, the method comprising:
   attaching an elastic device subcutaneously to the first penis side; and
   providing the elastic device with a stretch stop that limits elongation of the first penis side to an erection distance that is approximately equal to the affected length of the erect penis.

2. The method of claim 1, comprising attaching the elastic device subcutaneously to the first penis side between external skin of the penis and a tunica albuginea of the penis.

3. The method of claim 1, comprising providing an elastic band connected between a proximal support that is attachable to a base of the penis and a distal support that is attachable adjacent a corona of the penis.

4. The method of claim 3, comprising providing the elastic band with a second material that is attached to the elastic band, the second material configured to stop elongation of the elastic band.

5. A method of treating Peyronie's disease manifested in an erect penis having a first penis side with an unaffected length and a second penis side with an affected length that is shorter than the unaffected length, the method comprising:
   incising skin on the first penis side and accessing the tunica albuginea;
   creating an artificial erection in the penis;
   attaching a proximal end of an elastic device to a base of the penis on the first penis side;
   straightening the penis to reduce a curvature in the erect penis; and
   attaching a distal end of the elastic device adjacent to a corona of the penis on the first penis side to maintain the reduced curvature in the erect penis;
   wherein the elastic device includes a stretch stop that limits elongation of the first penis side to an erection distance that is approximately equal to the affected length of the erect penis.

* * * * *